United States Patent
Bosch Navarro et al.

(10) Patent No.: US 9,909,192 B2
(45) Date of Patent: Mar. 6, 2018

(54) CONTROL FOR VIRUS DETECTION ASSAYS BASED ON REVERSE-TRANSCRIPTION POLYMERASE CHAIN REACTION

(75) Inventors: Albert Bosch Navarro, Barcelona (ES); Rosa Maria Pinto Sole, Barcelona (ES)

(73) Assignee: UNIVERSIDAD DE BARCELONA, Barcelona (ES)

( * ) Notice: Subject to any disclaimer, the term of this patent is extended or adjusted under 35 U.S.C. 154(b) by 809 days.

(21) Appl. No.: 12/602,538

(22) PCT Filed: Jun. 1, 2007

(86) PCT No.: PCT/EP2007/055407
§ 371 (c)(1),
(2), (4) Date: Dec. 1, 2009

(87) PCT Pub. No.: WO2008/145197
PCT Pub. Date: Dec. 4, 2008

(65) Prior Publication Data
US 2010/0255459 A1    Oct. 7, 2010

(51) Int. Cl.
*C12Q 1/68* (2006.01)
*C12Q 1/70* (2006.01)

(52) U.S. Cl.
CPC ..................... *C12Q 1/701* (2013.01)

(58) Field of Classification Search
None
See application file for complete search history.

(56) References Cited

FOREIGN PATENT DOCUMENTS

FR    WO02095023    * 11/2002    ............. C12N 15/86

OTHER PUBLICATIONS

Costafreda et al. (Appl Environ. Micro, Jun. 2006, 72(6):3846-3855, IDS reference).*
Pan et al. (Antiviral Research, 2000, vol. 48, p. 39-47).*
Buck et al. (Biotechniques, 1999, 27, p. 528-536).*
Gregory et al. (Appl Environ Microbiol, 2006, 72(6):3960).*
Martin et al. (J Virol, 1996, 70(3):2027-2031).*
Cleland et al. (Vox Sanguinis, 1999, 76(3):170-174).*
Gordon et al. (J or Appl Microbiology, 2003, 95:536-544).*
Monpoeho 2004 et (Apply Envrion Microbiolg5434-5440.*
Monpoeho et al. (Appl. Environ. Microbiol., 2004, p. 5434-5440).*

(Continued)

*Primary Examiner* — Stephanie K Mummert
(74) *Attorney, Agent, or Firm* — Ipsilon USA, LLP

(57) ABSTRACT

A method for the accurate quantification of a virus in a sample, by reverse transcription polymerase chain reaction (RT-PCR), includes: adding a known concentration of a Mengo virus to the sample as control for the nucleic acids extraction step, the Mengo virus being a mutant strain with the same growth properties than those of the wild-type Mengo virus, and with non-pathogenic capacity; performing a nucleic acids extraction to obtain a nucleic acids suspension; analyzing the nucleic acids suspension by RT-PCR with primers and probes; quantifying the amplimers resulting from the RT-PCR; determining the concentration of the virus in the sample by comparison of the value obtained with an appropriate standard curve; and determining the concentration of the Mengo virus by comparison of the value obtained with an appropriate standard curve.

11 Claims, 2 Drawing Sheets

(56) References Cited

OTHER PUBLICATIONS

Drier et al. (Journal of Clinical Microbiology, 2005, 43(9):4551-4557, IDS reference).*
Costafreda, M Isabel et al., "Development Evaluation, and Standardization of a Real-Time TaqMan Reverse Transcription-PCR Assay for Quantification of Hepatitis A Virus in Clinical and Shellfish Samples", Applied and Environmental Microbiology, Jun. 2006, pp. 3846-3855, vol. 72, No. 6, XP002458580.
Database EMBL [Online], Jul. 23, 1993, "Mengo Virus Isolate M, Complete Genome", XP002458583.
Houde et al, "Comparative Evaluation of New TaqMan Real-Time Assays for the Detection of Hepatitis A Virus" Journal of VirologicalL Methods, Feb. 2, 2007, pp. 80-89, vol. 140, No. 1-2, Elsevier B.V., Amsterdam, NL, XP005870413, Abstract.
Jothikumar N. et al, "Development and Evaluation of a Broadly Reactive TaqMan Assay for Rapid Detection of Hepatitis A Virus", Applied and Environmental Microbiology, Jun. 2005, pp. 3359-3363, vol. 71, No. 6, XP002459673.
Guevremont et al, "Development of an Extraction and Concentration Procedure and Comparison of RT-PCR Primer Systems for the Detection of Hepatitis A Virus and Norovirus GII in Green Onions", Journal of Virological Methods, Jun. 2006, pp. 130-135, vol. 134, No. 1-2, Elsevier B.V., Amsterdam, NL, XP005408356, Abstract.
Costa-Mattioli M et al, "Quantification and Duration of Viraemia During Hepatitis A Infection as Determined by Real-Time RT-PCR", Journal of Viral Hepatitis, Mar. 2002, pp. 101-106, vol. 9, No. 2, XP002458582, Abstract.
International Search Report dated Dec. 4, 2007 from PCT/EP2007/055407.
Use of Bacteriophage MS2 as an Internal Control in Viral Reverse Transcription-PCR Assays (Dreier et al.) 2005.
Duplex real-time qRT-PCR for the detection of hepatitis A virus in water and raspberries using the MS2 bacteriophage as a process control (Blaise-Boisseau et al.) 2010.
Levels of male-specific RNA bacteriophage and *Escherichia coli* in molluscan bivalve shellfish from commerical harvesting areas (Dore et al.) 2003.
Chlorination of Indicator Bacteria and Viruses in Primary Sewage Effluent (Tree et al.) 2003.
F-specific RNA coliphages: occurrence, types, and survival in natural waters (Brion et al.) 2003.
Answer filed to the Canadian Patent Office May 7, 2014.

* cited by examiner

CONTROL FOR VIRUS DETECTION ASSAYS BASED ON REVERSE-TRANSCRIPTION POLYMERASE CHAIN REACTION

This invention relates to the field of molecular biology and its application in diagnostics. In particular, the invention relates to reagents to be used as controls in assays based on reverse-transcription polymerase chain reaction (referred as RT-PCR hereinafter).

BACKGROUND ART

Contamination of water sources and finished waters as well as food products by enteric viruses is a public health concern. Blood is another matrix that may contain different viruses with the associated health problems for the blood-manufacturing products industry. The use of RT-PCR for detection of viral contamination in environmental, food and blood-derivative samples is limited by a faulty RNA extraction or by the presence of several RT and PCR inhibitors that may lead to false negative results. Although RT-PCR assays are usually preceded by an inhibitor removal procedure, none of the known procedures can remove all of the inhibitors. The use of controls in RT-PCR has been reported for hepatitis A virus (HAV), Norwalk virus, rotavirus and enterovirus detection in shellfish, clinical samples, stool and sewage samples (cf. U. Sandhya et al., "Development of homologous viral internal controls for use in RT-PCR assays of waterborne enteric viruses", *J. Virological Methods* 2004, vol. 121, pp. 39-48).

In quantification assays based on RT-PCR, the general approach is based on the use of controls to measure the efficiency of those critical steps for the quantification: the nucleic acids extraction and the RT-PCR reactions. Further to RT and PCR inhibitors, another cause of false negatives in the RT-PCR is particularly a faulty RNA extraction. The control of the nucleic acids extraction generally involves the use of a non-pathogenic virus of similar structural characteristics to those of the target virus. For instance, since HAV belongs to the Picornaviridae family another member of the same family may be used to validate the behavior of HAV during the nucleic acids extraction procedures. The encephalomiocarditis virus (EMCV) has been proposed as a model for HAV in validation studies of HAV removal in blood products manufacturing by several agencies such as the European Agency for the Evaluation of Medicinal products or the American Food and Drug Administration. However, the use of this virus is hampered by its potential pathogenicity in several animals, including primates.

The development of sensitive reliable techniques for the accurate quantification of virus in many types of samples is required. Thus, the provision of reagents to be used as controls is desirable for the standardization and validation of such techniques.

SUMMARY OF THE INVENTION

The present invention provides a control to measure the efficiency of one of the critical steps for the quantification of a virus in assays based on RT-PCR, namely, the nucleic acids extraction.

Thus, an aspect of the invention relates to a quantification method of a virus in a sample, by RT-PCR, which comprises the following steps. First, a known concentration of a Mengo virus is added to the sample as control for the nucleic acids extraction step. This Mengo virus is a mutant strain with the same growth properties than those of the wild-type Mengo virus, and with non-pathogenic capacity. Then, a nucleic acids extraction to obtain a nucleic acids suspension is performed. In a third step, the nucleic acids suspension is analyzed by RT-PCR with primers that specifically bind to regions of the virus nucleic acid that are appropriate to generate an amplimer of the virus nucleic acid, and primers that specifically bind to regions of the Mengo virus that are appropriate to generate an amplimer of the Mengo virus. The amplimers resulting from this step are quantified. Finally, the concentration of the virus in the sample is determined by comparison of the value obtained from the analysis with an appropriate standard curve; and the concentration of the Mengo virus is determined by comparison of the value obtained from the analysis with an appropriate standard curve.

In a particular embodiment of the invention, the Mengo virus is the mutant strain $vMC_O$, as described in L. Martin et al., "Mutational analysis of the mengovirus poly(C) tract and surrounding heteropolymeric sequences" *J. Virol.* 1996, vol. 70, pp. 2027-31, which lacks the poly(C) tract from the 5' non-coding region of the wild-type Mengo virus. This mutant strain has the same growth properties than those of the wild-type Mengo virus and with no pathogenic capacity. The Mengo virus $vMC_0$ strain whose use as control is provided in this invention, represents a phenotypic variant of Mengo virus, avirulent in all animal species (murine and non-murine) so far tested, and used as a vaccine for a wide variety of hosts, including baboons, macaques and domestic pigs. In addition to its non-pathogenic phenotype, another important advantage of using this virus comes from the structure of the 5'NCR of its genomic RNA. This region is the most conserved of picornaviruses, and consequently is a good choice for the development of quantification techniques.

The RNA sequences that constitute the 5'NCR fold into complex multidomain structures which are involved in both translation and replication. The high conservation of the 5'NCR in all picornaviruses thus relies on its structural function. In fact, phylogenetic analyses of the 5'NCR of picornavirus reveal extensive structure-conserving substitutions within predicted stems, a high degree of sequence conservation in predicted loops, and clustering of regions with sequence divergence in spacer regions between domains.

To confirm the validity of the Mengo $vMC_0$ strain as control, a comparison analysis with respect to the behavior of the pHM175 43c strain of HAV was performed, and the results demonstrated a similar pattern for both viruses in both sera, fecal and shellfish samples. The election of HAV was due to its potential presence not only in food or water samples but also in blood products.

Mengo virus $vMC_0$ can be produced by transfection of a cDNA clone, $pMC_O$, into HeLa cells as previously described (cf. L. Martin et al., *J. Virol.* 1996, vol. 70, pp. 2027-31), and viral stocks can be thereafter produced in the same cells.

In another particular embodiment of the invention, the RT-PCR is a real-time RT-PCR, performed as known by those skilled in the art.

In particular embodiments, the virus in the sample to be quantified belongs to the family of non-enveloped (or naked) RNA virus, and more particularly to the family of ssRNA virus. In another embodiment, the virus in the sample (the target virus) belongs to the category of enteric viruses. This category comprises different viruses that are susceptible to be found as food and water contaminants. Examples of enteric viruses are Picornavirus (HAV) and Calicivirus (Norovirus, Hepatitis E, SRSV). Except for a few exceptions, the most well characterized foodborne viral outbreaks are restricted to norovirus (NoV) and HAV, which in consequence are nowadays the main targets for virus detection in water and food. Both HAV and NoV are single-stranded non-enveloped RNA viruses. NoV infections are very common and likely to become more so with new emerging strains described with increasing frequency. In contrast, HAV, with its single serotype so far described, and a reliable vaccine available appears as a potentially eradicable infection. Mengo virus is an appropriate extraction control for non-enveloped viruses in food, clinical or environmental samples.

In particular embodiments, concentrations of Mengo virus of around $10^5$ infectious units/ml are added in case of clinical samples, sera and stool, while $10^6$ infectious units/g are employed for shellfish samples.

Another aspect of the invention relates to a quantification method of a virus in a sample, by RT-PCR, which comprises several steps such as the nucleic acids extraction and the RT-PCR quantification. Previous to the nucleic acids extraction step, a known concentration of a Mengo virus is added to the sample. This Mengo virus is a mutant strain with the same growth properties than those of the wild-type Mengo virus and with no pathogenic capacity. Then, the nucleic acids extraction is performed to obtain the nucleic acids suspension. The efficiency of the nucleic acids extraction is measured by comparing the genome copies of the added Mengo virus and that of the recovered Mengo virus. The titer of genome copies of the Mengo virus is obtained by extrapolation from an standard curve which is made with Mengo virus titrated by infectivity. The genome copies are titrated by a real-time TaqMan RT-PCR based on the amplification of a fragment of the 5' non-coding region (5'NCR) of the Mengo virus genome. In particular, the amplification is made with primers with sequences which comprise SEQ ID NO: 4-5 or their complementary sequences. Particularly the primers have the sequences SEQ ID NO: 4-5. In another embodiment, the fluorescent probe for the quantification of the Mengo virus is the SEQ ID NO: 6 labeled with the 5' 6-carboxyfluorescein (FAM) and modified with a 3' minor groove binder (MGB). In another embodiment, the real-time RT-PCR is carried out in a one-step format under the following conditions: 1 hour at 50° C. for the reverse transcription reaction, 10 minutes at 95° C. as a hot start and 45 cycles each of 15 seconds at 95° C. for denaturation, 1 minute at 60° C. for annealing and 1 minute at 70° C. for extension.

Particular quantification methods which include the control of the RNA extraction of the invention are described herein. The method generally comprises adding firstly a known concentration of the Mengo virus of the invention to the sample and performing a nucleic acids extraction to obtain a nucleic acids suspension. Then at least two subsamples of the nucleic acids suspension, here referred as 2 and 3, are taken and the subsamples are analyzed by RT-PCR with reaction mixtures that comprise primers that specifically bind to regions of the virus nucleic acid that are appropriate to generate an amplimer of the virus nucleic acid, primers that specifically bind to regions of the Mengo virus that are appropriate to generate an amplimer of the Mengo virus, and detectable labeled probes that specifically binds to the amplimers resulting from the RT-PCRs. Then, relevant concentrations in each subsample is determined by comparison of the values obtained from the analysis with two standard curves, here referred as 2 and 3: an standard curve 2, being used for the quantification of the virus, and being made with an appropriate nucleic acid molecule (preferably a dsDNA corresponding to the virus amplimer) titrated by means of the optical density; and an standard curve 3, being used for the quantification of Mengo virus, and being made with Mengo virus titrated by infectivity. Finally the efficiency of the nucleic acids extraction is determined by comparison of the detected Mengo virus in the subsample 3 with the added Mengo virus.

Preferably, a third subsample of the nucleic acids suspension is taken for analysis. To this subsample (referred herein as 1), a known concentration of a ssRNA molecule is added for the control of the RT-PCR efficiency. The three subsamples are analyzed by RT-PCR and the concentration in each subsample is determined. In case of the subsample 1, the concentration is determined by comparison of the value obtained from the analysis with another standard curves, here referred as 1, being used for the quantification of the single stranded RNA molecule for the control of the RT-PCR efficiency, and being made with the same molecule titrated by means of the optical density. Finally, the efficiency of the RT-PCR is determined by comparison of the number of the ssRNA molecules detected, by substracting the number of virus genomes quantified in the subsample 2 from the sum of virus plus the ssRNA molecules in the subsample 1, with the number of ssRNA molecules added.

Unless otherwise defined, all technical and scientific terms used herein have the same meaning as commonly understood by those ordinary skilled in the art. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following particular embodiments, drawings and sequence listing are provided by way of illustration and are not intended to be limiting of the present invention. In the following sections, the invention is illustrated by its application in the quantification of HAV in clinical and shellfish samples by a real-time RT-PCR assay.

DETAILED DESCRIPTION OF PARTICULAR EMBODIMENTS

Virus and Primer/Probe Set Selection

Figure 1:
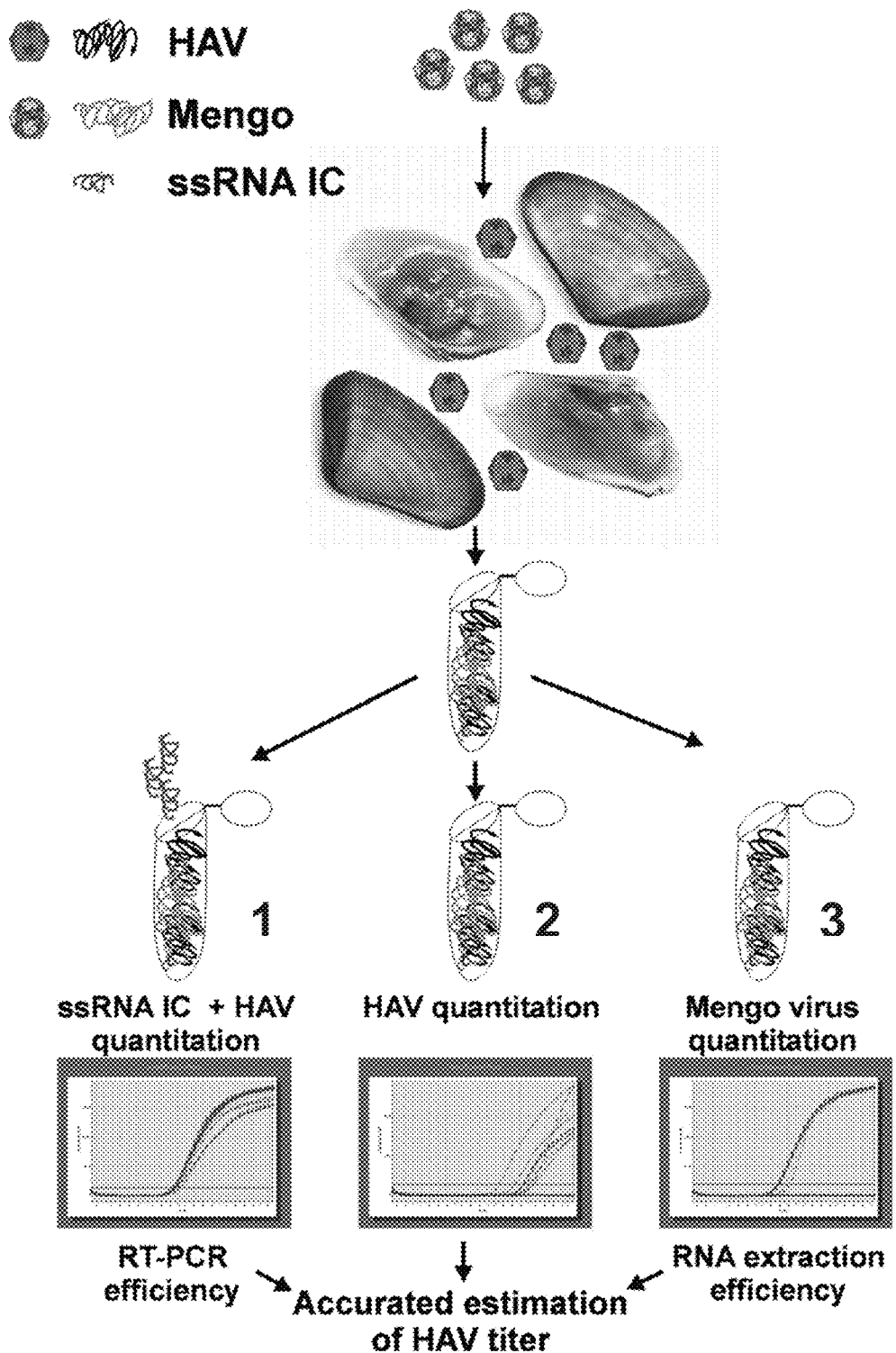
FIG. 1 shows the proposed standardized procedure for an accurate estimation of HAV genome copies in food or clinical samples. The whole test involves the generation of three different standard curves: one for the quantification of Mengo virus (made with Mengo virus titrated by infectivity), another for the quantification of a ssRNA molecule used as a control of the RT-PCR (made with a ssRNA molecule titrated by means of the $OD_{260}$ and obtained by in vitro transcription of a cloned fragment corresponding to the amplimer) and a third for the quantification of HAV (made with the dsDNA molecule or amplimer titrated again by means of the $OD_{260}$). All these standard curves are obtained in a single plate, which additionally contains wells devoted to the calculation of extraction and enzymes efficiencies, as well as the samples to be tested, all under exactly the same conditions. 1, 2 and 3 refer to the three subsamples devoted to the amplification of the Mengo virus, to the ssRNA and to HAV, respectively.

Infectious Mengo virus was obtained after transfection of a cDNA clone, $pMC_0$ (kindly provided by Prof. Ann Palmenberg, University of Wisconsin), into HeLa cells as previously described (cf. L. Martin et al., *J. Virol.* 1996, vol. 70, pp. 2027-31), and viral stocks were thereafter produced in the same cells.

The selection of a highly conserved primer/probe set was the first step on the design of a real-time RT-PCR for viral quantification. The most conserved region of Mengo virus corresponds to the 5'NCR and primers and probe for the real-time RT-PCR were chosen from this region. The reverse primer Mengo209 REV (5'GAAGTAACATATAGACA-GACGCACAC3', SEQ ID NO: 4) and the forward primer Mengo110 FW (5'GCGGGTCCTGCCGAAAGT3', SEQ ID NO: 5) were used for the RT-PCR amplification. The fluorescent probe for the quantification was the Mengo147 (5'ATCACATTACTGGCCG AAGC3', SEQ ID NO: 6) labeled with the 5' 6-carboxyfluorescein (FAM) and modified with a 3' minor groove binder (MGB).

Real-Time RT-PCR Tagman Assay for Mengo Virus

A one-step reaction was performed. The concentration of primers, probe, and $Mg^{2+}$ was optimized at 0.6 µM, 0.25 µM, and 3 mM, respectively, in a final volume of 25 µl containing 5 µl of sample. The temperature-time-program was as follows: 1 hour at 50° C. for the RT reaction, 10 min at 95° C. as a hot start and 45 cycles each of 15 sec at 95° C. for denaturation, 1 min at 60° C. for annealing and 1 min at 70° C. for extension. The fluorescence was measured at the end of each cycle.

Mengo Virus as a Nucleic Acids Extraction Control

Important issues must be solved before conducting the whole test such as the determination of the optimal amount of Mengo virus to be added. Three different concentrations of Mengo virus were tested in serum, stool suspensions and shellfish digestive tissues (TABLE 1), ranging from $8.6 \times 10^6$ to $8.6 \times 10^2$ infectious units/ml in the two former cases and from $1.0 \times 10^6$ to $1.0 \times 10^2$ infectious units/g of digestive tissues in the third type of sample. Each spiked sample was extracted twice and each nucleic acids suspension was titrated by real-time TaqMan RT-PCR. Although a certain level of variability was observed in all types of samples, this variability was indeed more related to the nature of the particular samples rather than to the concentration of viruses added. In view of the low viral nucleic acids recovery efficiencies (TABLE 1), mostly in shellfish samples, concentrations of Mengo virus of around $10^5$ infectious units/ml were selected for clinical samples, sera and stool, while $10^6$ infectious units/g were employed for shellfish samples. In an attempt to discard the possibility of a different behavior of Mengo virus and that of those virus to test, comparative experiments with the behavior of HAV as model virus were performed. During the extraction procedures the pHM175 43c strain of HAV was added at different concentrations to the different types of samples (TABLE 2). The extraction efficiency was similar for both viruses (Mengo virus and HAV) thus validating the use of the Mengo virus control.

The proposed method based on the use of Mengo virus as a nucleic acids extraction control was applied to the quantification of experimentally contaminated clinical and shellfish samples as well as to naturally contaminated clinical and shellfish samples.

Viral RNA Extraction from Clinical and Shellfish Samples

Clinical samples included stool and sera samples from patients affected of hepatitis A. Additionally, stool and sera samples from patients non-affected of hepatitis A were experimentally contaminated with the pHM175 43c HAV strain. Stools were suspended (10%, wt/vol) in phosphate-buffered saline containing 2M $NaNO_3$, 1% BSA (FractionV) and 0.1% Triton X-100 (pH 7.2), pelleted at 1000×g for 5 min. At this point the Mengo virus control was added at a concentration of $10^5$ infectious virus/ml and nucleic acids extracted from 150 µl of the resulting supernatant using the RNeasy Plant Mini Kit (QIAGEN). Nucleic acids were purified from 150 µl of serum, to which the Mengo virus control was added at a concentration of $10^5$ infectious virus/ml, by using the NucleoSpin RNA Virus (Macherey-Nagel). Frozen samples of clams directly associated with an outbreak of hepatitis A, were analyzed. Processing of shellfish was performed essentially by the method described by Atmar et al (cf. R. L. Atmar et al., "Detection of Norwalk virus and hepatitis A virus in shellfish tissues with the PCR" Appl. Environ. Microbiol. 1995, vol. 61, pp. 3014-8). Briefly, the stomachs and digestive diverticula were dissected from the clams and subjected to high-speed homogenization (Sorval OCI Omni mixer, Omni Intl., Waterbury, Conn., USA). The Mengo virus control was added at a concentration of $10^6$ infectious virus/ml to the homogenates. Viruses were extracted from these homogenates (corresponding to 1.5 g of shellfish tissue) by sequential extractions with chloroform-butanol and Cat-Floc T (Calgon Corp., Elwood, Pa., USA), and concentrated by polyethylene-glycol precipitation. Nucleic acids from these concentrates were extracted with the RNeasy Plant Mini Kit (QIAGEN) following the manufacturer's instructions.

Accurate Quantification of HAV in Clinical Samples Through the Use of the Mengo Virus Extraction Control The primers and probe for the quantification of HAV were HAV240 (5'GGAGAGCCCTGGAAGAAAG3') (SEQ ID NO: 2), HAV68 (5'TCACCGCCGTTTGCCTAG3') (SEQ ID NO: 1) and the probe HAV150(−) (5'CCTGAACCT-GCAGGAATTAA3') (SEQ ID NO: 3).

Figure 2:
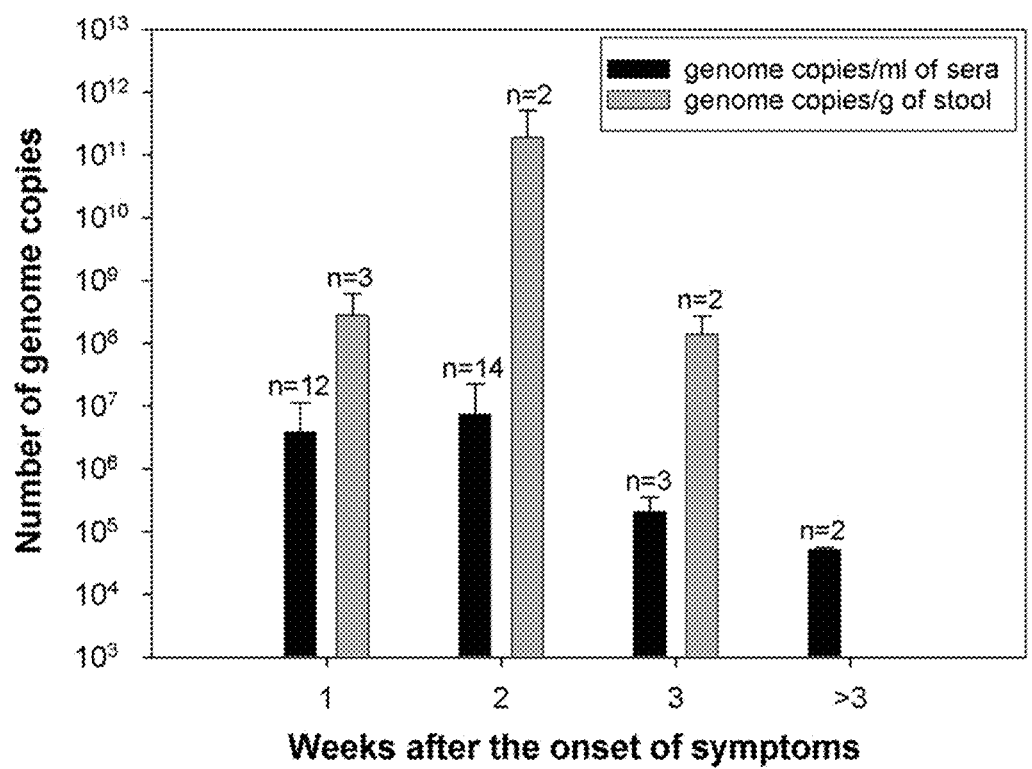
FIG. 2 shows the time-course of HAV genome copies in sera and feces from patients of a shellfish-borne outbreak, accurately titrated by using the Mengo virus as a nucleic acids extraction control.

The use of the Mengo virus control for the accurate quantification of HAV in clinical samples from patients suffering from acute hepatitis and diagnosed positive for hepatitis A by means of IgM positivity was assessed. The HAV quantitative results (TABLE 3) revealed a high and long lasting viremia, with the peak occurring at two weeks after the onset of symptoms (FIG. 2). Regarding the titers detected in feces, the results revealed numbers higher than expected (TABLE 4) with a peak showing up again around two weeks after the onset of symptoms (FIG. 2).

Accurate Quantification of HAV in Shellfish Samples Through the Use of the Mengo Virus Extraction Control The same approach was applied for the quantification of the HAV present in the shellfish samples associated with an HAV outbreak (TABLE 5). Three out of seven tested samples could be quantified, showing estimated titers ranging from $7.5 \times 10^3$ to $7.3 \times 10^5$ HAV genomes per gram of digestive tissues, or around $1 \times 10^3$ to $1 \times 10^5$ per g of clam. The rest of the samples, were either negative for viruses or contained virus levels below the detection limit, which strongly depends on the efficiency of the extraction procedure.

TABLE 1

Validation of Mengo virus control as standard for the determination of nucleic acids extraction efficiency.

| Sample | Spiked Mengo Virus[a] | Recovered Mengo Virus[b] | NA Extraction Efficiency (%) |
|---|---|---|---|
| Serum-1 | $8.6 \times 10^6$ | $(1.1 \pm 1.4) \times 10^7$ | $100.0 \pm 0.0$ |
|  | $8.6 \times 10^4$ | $(3.6 \pm 1.0) \times 10^5$ | $100.0 \pm 0.0$ |
|  | $8.6 \times 10^2$ | $(3.6 \pm 2.3) \times 10^3$ | $100.0 \pm 0.0$ |
| Serum-2 | $8.6 \times 10^6$ | $(1.1 \pm 3.7) \times 10^6$ | $12.3 \pm 4.4$ |
|  | $8.6 \times 10^4$ | $(2.5 \pm 1.6) \times 10^4$ | $28.8 \pm 19.0$ |
|  | $8.6 \times 10^2$ | $(2.6 \pm 1.9) \times 10^2$ | $30.7 \pm 21.7$ |
| Stool-1 | $8.6 \times 10^6$ | $(3.4 \pm 0.4) \times 10^6$ | $39.5 \pm 4.9$ |
|  | $8.6 \times 10^4$ | $(5.1 \pm 2.2) \times 10^4$ | $59.0 \pm 25.4$ |
|  | $8.6 \times 10^2$ | $(4.3 \pm 2.3) \times 10^2$ | $49.3 \pm 25.9$ |
| Stool-2 | $8.6 \times 10^6$ | $(3.0 \pm 1.3) \times 10^6$ | $34.6 \pm 15.3$ |
|  | $8.6 \times 10^4$ | $(3.5 \pm 6.6) \times 10^3$ | $40.0 \pm 7.6$ |
|  | $8.6 \times 10^2$ | $(9.3 \pm 10.0) \times 10^2$ | $65.7 \pm 48.4$ |
| Shellfish | $1.0 \times 10^6$ | $(9.1 \pm 9.2) \times 10^2$ | $0.1 \pm 0.1$ |
|  | $1.0 \times 10^4$ | $(2.2 \pm 0.7) \times 10^1$ | $0.2 \pm 0.1$ |
|  | $1.0 \times 10^2$ | ND[c] | — |

[a]The inocula added are expressed as $TCID_{50}$/ml for sera and stool suspensions, or $TCID_{50}$/g of hepatopancreas for shellfish.
[b]Each spiked sample was extracted twice and each nucleic acids suspension was titrated by real-time TaqMan RT-PCR using a standard curve made by means of Mengo virus infectious units.
[c]ND: Not detected.

TABLE 2

Comparative behavior of infectious Mengo virus and infectious HAV in the nucleic acids extraction.

| Sample | Spiked Mengo Virus[a] | Recovered Mengo Virus[b] | NA Extraction Efficiency (%) | Spiked HAV[c] | Recovered HAV[d] | NA Extraction Efficiency (%) |
|---|---|---|---|---|---|---|
| Serum | $8.6 \times 10^6$ | $1.3 \times 10^5$ | 1.5 | $2.0 \times 10^6$ | $1.1 \times 10^5$ | 5.5 |
|  | $8.6 \times 10^4$ | $1.0 \times 10^4$ | 11.6 | $2.0 \times 10^4$ | $6.7 \times 10^2$ | 3.3 |
| Stool | $8.6 \times 10^6$ | $2.1 \times 10^6$ | 23.8 | $2.0 \times 10^6$ | $2.8 \times 10^5$ | 14.0 |
|  | $8.6 \times 10^4$ | $3.0 \times 10^4$ | 34.6 | $2.0 \times 10^4$ | $1.4 \times 10^3$ | 7.0 |
| Shellfish | $1.0 \times 10^6$ | $1.6 \times 10^3$ | 0.2 | $2.0 \times 10^6$ | $4.0 \times 10^3$ | 0.2 |
|  | $1.0 \times 10^4$ | $2.7 \times 10^0$ | 0.3 | $2.0 \times 10^4$ | $3.3 \times 10^1$ | 0.2 |

[a]The inocula added are expressed as $TCID_{50}/ml$ for sera and stool suspensions, or $TCID_{50}/g$ of hepatopancreas for shellfish.
[b]Each spiked sample was extracted and the nucleic acids suspension titrated by real-time TaqMan RT-PCR using a standard curve made by means of Mengo virus infectious units.
[c]The pHM175 43c strain of HAV was added and virus titers are expressed as $TCID_{50}/ml$ for sera and stool suspensions, or $TCID_{50}/g$ for shellfish.
[d]Each spiked sample was extracted and the nucleic acids suspension titrated by real-timeTaqMan RT-PCR using a standard curve made by means of HAV infectious units.

TABLE 3

Quantification of HAV in sera samples from patients from an outbreak.

| Sample Genotype | Spiked Mengo Virus[a] | R. Mengo Virus[b] | NA E.E (%) | HAV Crude Sample[c] | HAV Final Estimate[c] |
|---|---|---|---|---|---|
| 1 (IA) | $1.3 \times 10^5$ | $3.2 \times 10^4$ | 24.7 | $1.6 \times 10^5$ | $6.4 \times 10^5$ |
| 2 (IA) | $1.3 \times 10^5$ | $5.4 \times 10^4$ | 51.9 | $3.2 \times 10^8$ | $6.2 \times 10^8$ |
| 3 (IA) | $1.3 \times 10^5$ | $5.7 \times 10^4$ | 48.5 | $3.2 \times 10^7$ | $6.6 \times 10^7$ |
| 1 (IB) (1 week[d]) | $1.3 \times 10^5$ | $6.6 \times 10^4$ | 50.0 | $4.8 \times 10^5$ | $9.6 \times 10^5$ |
| 2 (IB) (1 week) | $1.3 \times 10^5$ | $1.7 \times 10^4$ | 13.0 | $1.4 \times 10^5$ | $1.1 \times 10^6$ |
| 3 (IB) (2 weeks) | $1.3 \times 10^5$ | $6.6 \times 10^3$ | 5.0 | $1.9 \times 10^6$ | $3.8 \times 10^7$ |
| 4 (IB) (2 weeks) | $1.3 \times 10^5$ | $1.5 \times 10^4$ | 11.5 | $9.2 \times 10^5$ | $8.0 \times 10^6$ |
| 5 (IB) (3 weeks) | $1.3 \times 10^5$ | $1.7 \times 10^4$ | 13.0 | $7.4 \times 10^4$ | $5.6 \times 10^5$ |
| 6 (IB) (3 weeks) | $1.3 \times 10^5$ | $3.8 \times 10^4$ | 28.5 | $6.8 \times 10^4$ | $2.4 \times 10^5$ |
| 7 (IB) (6 weeks) | $1.3 \times 10^5$ | $8.6 \times 10^3$ | 6.5 | $3.1 \times 10^3$ | $4.8 \times 10^4$ |
| 8 (IB) (6 weeks) | $1.3 \times 10^5$ | $6.3 \times 10^4$ | 48.5 | $2.6 \times 10^4$ | $5.4 \times 10^4$ |

R. means recovered.
E.E. means Extraction Efficiency.
[a]The inocula added are expressed as $TCID_{50}/ml$ of serum.
[b]Each spiked sample was extracted and the nucleic acids suspension was titrated by real-time TaqMan RT-PCR using a standard curve made by means of Mengo virus infectious units.
[c]The titer is expressed as the number of genome copies per ml of serum.
[d]Week after the onset of symptoms at which the samples were taken.

TABLE 4

Quantification of HAV in fecal samples from patients with acute hepatitis A from an outbreak.

| Sample | Spiked Mengo Virus[a] | R. Mengo Virus[b] | NA E.E. (%) | Spiked ssRNA[c] | R. ssRNA[d] | RT-PCR Efficiency (%) | HAV Crude Sample[e] | HAV Final Estimate[e] |
|---|---|---|---|---|---|---|---|---|
| 1 (1 week[f]) | $1.3 \times 10^5$ | $2.8 \times 10^4$ | 21.0 | $1.5 \times 10^8$ | $9.6 \times 10^7$ | 64.9 | $1.1 \times 10^7$ | $5.1 \times 10^8$ |
| 2 (1 week) | $1.3 \times 10^5$ | $2.7 \times 10^3$ | 2.1 | $1.5 \times 10^8$ | $5.2 \times 10^7$ | 35.1 | $9.2 \times 10^4$ | $4.4 \times 10^7$ |
| 3 (1 week) | $1.3 \times 10^5$ | $3.5 \times 10^4$ | 26.5 | $1.5 \times 10^8$ | $1.3 \times 10^7$ | 8.6 | $3.6 \times 10^4$ | $4.2 \times 10^6$ |
| 4 (2 week) | $1.3 \times 10^5$ | $8.0 \times 10^3$ | 6.0 | $1.5 \times 10^8$ | $1.0 \times 10^6$ | 1.0 | $2.2 \times 10^7$ | $2.2 \times 10^{10}$ |
| 5 (2 week) | $1.3 \times 10^5$ | $1.3 \times 10^3$ | 1.0 | $1.5 \times 10^8$ | $1.0 \times 10^8$ | 70.3 | $5.6 \times 10^7$ | $5.6 \times 10^{11}$ |
| 6 (3 week) | $1.3 \times 10^5$ | $2.8 \times 10^3$ | 2.1 | $1.5 \times 10^8$ | $2.0 \times 10^7$ | 21.6 | $5.6 \times 10^5$ | $2.7 \times 10^8$ |
| 7 (3 week) | $1.3 \times 10^5$ | $5.1 \times 10^4$ | 38.0 | $1.5 \times 10^8$ | $9.6 \times 10^6$ | 6.5 | $4.6 \times 10^4$ | $7.1 \times 10^6$ |

R. means recovered.
E.E. means Extraction Efficiency.
[a]The inocula added are expressed as $TCID_{50}/ml$ of fecal suspension.
[b]Each spiked sample was extracted and the nucleic acids suspension was titrated by real-time TaqMan RT-PCR using a standard curve made by means of Mengo virus infectious units.
[c]RT-PCR inhibition is controlled by means of a ssRNA control. In the previous table due to the lack of inhibition of the RT-PCR this data is not shown for the sake of clarity. However, in stool samples RT-PCR inhibition was observed after the nucleic acids extraction and thus this information is depicted. The inocula added are expressed as the number of molecules of the ssRNA control per ml of nucleic acids suspension.
[d]Each spiked nucleic acids suspension was titrated by a TaqMan Real-time RT-PCR using a standard curve made by means of HAV-derived ssRNA molecules estimated from the $OD_{260}$ readings.
[e]The titer is expressed as the number of genome copies per g of feces.
[f]Week after the onset of symptoms at which the samples were taken.

TABLE 5

Quantification of HAV in shellfish samples associated with an outbreak.

| Sample | Spiked Mengo Virus[a] | R. Mengo Virus[b] | NA E.E. (%) | HAV Crude Sample[c] | HAV Final Estimate[c] |
|---|---|---|---|---|---|
| 1 | $8.6 \times 10^5$ | $8.6 \times 10^2$ | 0.10 | ND[d] | — |
| 2 | $8.6 \times 10^5$ | $6.4 \times 10^2$ | 0.07 | $3.5 \times 10^1$ | $6.5 \times 10^4$ |
| 3 | $8.6 \times 10^5$ | $1.1 \times 10^3$ | 0.13 | ND | — |
| 4 | $8.6 \times 10^5$ | $1.3 \times 10^3$ | 0.15 | $1.1 \times 10^3$ | $7.3 \times 10^5$ |
| 5 | $8.6 \times 10^5$ | $8.0 \times 10^2$ | 0.09 | $4.4 \times 10^0$ | $7.5 \times 10^3$ |
| 6 | $8.6 \times 10^5$ | $5.9 \times 10^2$ | 0.07 | ND | — |
| 7 | $8.6 \times 10^5$ | $1.2 \times 10^3$ | 0.14 | ND | — |

[a]The inocula added are expressed as $TCID_{50}/g$ of hepatopancreas.
[b]Each spiked sample was extracted and the nucleic acids suspension was titrated by real-time TaqMan RT-PCR using a standard curve made by means of Mengo virus infectious units.
[c]The titer is expressed as the number of genome copies per g of hepatopancreas.
[d]Not Detected (<6.66 copies per g of hepatopancreas, assuming a 100% efficiency for both extraction and RT-PCR).

The invention claimed is:

1. A method of quantifying a non-enveloped RNA virus in a sample, selected from the group consisting of food, clinical and environmental samples, said method comprising the steps of:
(i) adding a control to the sample, said control comprising a known concentration of Mengo virus, the Mengo virus being a mutant strain vMC$_0$ non-pathogenic capacity;
(ii) extracting nucleic acid from the sample of step (i) to obtain a nucleic acid suspension;
(iii) analyzing the nucleic acid suspension by real-time reverse transcription-polymerase chain reaction (RT-PCR) with (a) primers that specifically bind to regions of the non-enveloped RNA virus nucleic acid that are appropriate to generate an amplimer of the RNA virus nucleic acid, and (b) primers that specifically bind to regions of the Mengo virus nucleic acid that are appropriate to generate an amplimer of the Mengo virus nucleic acid;
(iv) quantifying the amplimers resulting from step (iii) to obtain a value for the non-enveloped RNA virus and for the Mengo virus;
(v) determining a concentration of the non-enveloped RNA virus in the sample by comparing the value for the non-enveloped RNA virus obtained from step (iv) with an appropriate standard curve; and
(vi) determining a concentration of the Mengo virus by comparing the value for the Mengo virus obtained from step (v) with an appropriate standard curve,
wherein the Mengo virus vMC$_0$ serves as a control for a combined efficiency of the nucleic acid extraction step (ii) and the RT-PCR analysis step (iii).

2. The method according to claim 1, wherein the non-enveloped RNA virus is a single-stranded RNA virus.

3. The method according to claim 2, wherein the non-enveloped RNA virus is an enteric virus.

4. The method according to claim 1, wherein the primers that specifically bind to regions of the Mengo virus comprise a primer of SEQ ID NO: 4 or its complementary sequence and a primer of SEQ ID NO: 5 or its complementary sequence.

5. The method according to claim 4, wherein the primers consist of a primer consisting of SEQ ID NO: 4 and a primer consisting of SEQ ID NO: 5.

6. The method according to claim 1, wherein the sample is a clinical sample, and the known concentration of Mengo virus added to the sample is $10^5$ infectious units/ml.

7. The method according to claim 1, wherein the sample is shellfish, and the known concentration of Mengo virus added to the sample is $10^6$ infectious units/ml.

8. A method of quantifying a non-enveloped RNA virus in a sample, selected from the group consisting of food, clinical and environmental samples, said method comprising the steps of:
(i) adding a control to the sample, said control comprising a known concentration of Mengo virus, the Mengo virus being a mutant strain vMC$_0$ with no pathogenic capacity;
(ii) extracting nucleic acid from the sample of step (i) to obtain a nucleic acid suspension;
(iii) taking two subsamples of the nucleic acid suspension, here referred to as subsample 2 and subsample 3;
(iv) analyzing each of the two subsamples by real-time reverse transcription-polymerase chain reaction (RT-PCR),
(a) subsample 2 being analyzed with a reaction mixture comprising (a1) primers that specifically bind to regions of the non-enveloped RNA virus nucleic acid that is appropriate to generate an amplimer of the RNA virus nucleic acid, and (a2) detectably labeled probes that specifically bind to said amplimer,
(b) subsample 3 being analyzed with a reaction mixture comprising (b1) primers that specifically bind to regions of the Mengo virus nucleic acid that is appropriate to generate an amplimer of the Mengo virus nucleic acid, and (b2) detectably labeled probes that specifically bind to said amplimer;
(v) determining the concentration of non-enveloped RNA virus or Mengo virus in each subsample by comparing values obtained from the analysis in step (iv) with appropriate standard curves, here referred to as standard curve 2 and standard curve 3,
standard curve 2 being used to quantify the non-enveloped RNA virus, and being made with an appropriate nucleic acid molecule titrated by optical density; and
standard curve 3 being used to quantify the Mengo virus, and being made with Mengo virus titrated by infectivity; and
(vi) determining a combined efficiency of the nucleic acid extraction of step (ii) and the RT-PCR analysis of step (iv) by comparing the quantified Mengo virus of step (v) in the subsample 3 with the known concentration of Mengo virus added to the sample in step (i).

9. A method of quantifying a non-enveloped RNA virus in a sample, selected from the group consisting of food, clinical and environmental samples, said method comprising the steps of:
(i) adding a control to the sample, said control comprising a known concentration of Mengo virus, the Mengo virus being a mutant strain vMC$_0$ with non-pathogenic capacity;

(ii) extracting nucleic acid from the sample of step (i) to obtain a nucleic acid suspension;

(iii) taking at least three subsamples of the nucleic acid suspension, here referred to as subsamples 1, 2 and 3, and adding to the subsample 1 a known concentration of a single-stranded RNA molecule as a control for RT-PCR efficiency;

(iv) analyzing each of the at least three subsamples by real-time RT- PCR with reaction mixtures that comprise (a) primers that specifically bind to regions of the non-enveloped RNA virus nucleic acid that are appropriate to generate an amplimer of the non-enveloped RNA virus nucleic acid, (b) primers that specifically bind to regions of the Mengo virus nucleic acid that are appropriate to generate an amplimer of the Mengo virus nucleic acid, and (c) detectable labeled probes that specifically bind to said non-enveloped RNA virus and Mengo virus amplimers;

(v) determining the concentration of the single stranded RNA molecule, the non-enveloped RNA virus and the Mengovirus in each subsample by comparing the values obtained from the RT-PCR analysis in step (iv) with appropriate standard curves, here referred to as standard curves 1, 2 and 3, standard curve 1 being used to quantify the single-stranded RNA molecule for the control of the RT-PCR efficiency, the standard curve 1 being generated with concentrations of the same single-stranded RNA molecule titrated by optical density;

standard curve 2 being used to quantify the non-enveloped RNA virus, the standard curve 2 being generated with concentrations of the appropriate non-enveloped RNA virus nucleic acid molecule titrated by optical density; and standard curve 3 being used to quantify the Mengo virus, the standard curve 3 being generated with Mengo virus titrated by infectivity; and (vi) determining the efficiency of the nucleic acid extraction step (ii) by comparing the concentration of the Mengo virus quantified in the subsample 3 with the known concentration of Mengo virus added to the sample in step (i), and determining the efficiency of the RT-PCR analysis step (iv) by comparing the single-stranded RNA molecules quantified in step (v), by subtracting the number of non-enveloped RNA virus genomes quantified in the subsample 2 from the sum of non-enveloped RNA virus plus the single stranded RNA molecules in the subsample 1, with the number of single-stranded RNA molecules added.

10. The method according to claim 8, wherein the non-enveloped RNA virus is a single-stranded RNA virus.

11. The method according to claim 10, wherein the non-enveloped RNA virus is an enteric virus.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Synthetic forward primer HAV68

<400> SEQUENCE: 1
tcaccgccgt ttgcctag                                              18

<210> SEQ ID NO 2
<211> LENGTH: 19
<212> TYPE: DNA
<213> ORGANISM: Artificial Sequence
<220> FEATURE:
<223> OTHER INFORMATION: Synthetic reverse primer HAV240

<400> SEQUENCE: 2
ggagagccct ggaagaaag                                             19

<210> SEQ ID NO 3
<211> LENGTH: 20
<212> TYPE: DNA
<213> ORGANISM: Artificial Sequence
<220> FEATURE:
<223> OTHER INFORMATION: Synthetic probe HAV150(-)

<400> SEQUENCE: 3
cctgaacctg caggaattaa                                            20

<210> SEQ ID NO 4
<211> LENGTH: 26
<212> TYPE: DNA
<213> ORGANISM: Artificial Sequence
<220> FEATURE:
<223> OTHER INFORMATION: Synthetic reverse primer Mengo209 REV

<400> SEQUENCE: 4
gaagtaacat atagacagac gcacac                                     26

<210> SEQ ID NO 5
<211> LENGTH: 18
<212> TYPE: DNA
<213> ORGANISM: Artificial Sequence
<220> FEATURE:
<223> OTHER INFORMATION: Synthetic forward primer Mengo110 FW

```
<400> SEQUENCE: 5
gcgggtcctg ccgaaagt                                                18

<210> SEQ ID NO 6
<211> LENGTH: 20
<212> TYPE: DNA
<213> ORGANISM: Artificial Sequence
<220> FEATURE:
<223> OTHER INFORMATION: Synthetic probe Mengo147

<400> SEQUENCE: 6
atcacattac tggccgaagc                                              20
```